United States Patent [19]

Schafer

[11] Patent Number: 5,717,142
[45] Date of Patent: Feb. 10, 1998

[54] ULTRASOUND IMAGE FREEZING APPARATUS AND METHOD FOR ANIMAL BACKFAT MEASURING INSTRUMENTS

[76] Inventor: Mark Evan Schafer, 165 Percy Ct., Norristown, Pa. 19401

[21] Appl. No.: 586,002

[22] Filed: Jan. 16, 1996

[51] Int. Cl.⁶ ................................................. G01N 29/06
[52] U.S. Cl. ........................ 73/597; 73/629; 128/660.03
[58] Field of Search ........................................ 345/169, 156; 340/936, 937, 438, 439; 128/660.03; 73/597, 599, 620, 629, 631

[56] References Cited

U.S. PATENT DOCUMENTS

| | | | |
|---|---|---|---|
| 4,359,055 | 11/1982 | Carlson | 73/609 |
| 4,359,056 | 11/1982 | Carlson | 73/631 |
| 4,567,768 | 2/1986 | Satoh | 73/606 |
| 4,646,748 | 3/1987 | Fujii | 73/599 |
| 4,671,289 | 6/1987 | Gainsley | 128/660 |
| 4,700,711 | 10/1987 | Carlson | 73/612 |
| 4,779,623 | 10/1988 | Suminomo | 73/597 |

*Primary Examiner*—Christine K. Oda
*Attorney, Agent, or Firm*—John Shaw Stevenson

[57] ABSTRACT

An apparatus to determine if an echo signal shown on a multi-echo analog display unit that is produced by an ultrasonic animal backfat measuring and analyzing instrument is an accurate indication of the depth of backfat under measurement. This display unit has a small hand retainable switch to freeze the signal under measurement to allow the analyzing portion of the instrument to send a signal to the display unit to inscribe a graphical overlay indication upon the echo signal. If the overlay indicator passes through the strongest one of the echo signals then the echo signal is thereby identified as being an accurate measurement of the animal backfat. If it does not, this indicates that something has interfered with this signal and it is therefore inaccurate.

10 Claims, 8 Drawing Sheets

ULTRASOUND IMAGE FREEZING APPARATUS AND METHOD FOR ANIMAL BACKFAT MEASURING INSTRUMENTS

DESCRIPTION OF PRIOR ART

The primary advantages of the system over prior art devices are (1) a freeze control switching unit is used that allows the trace of an ultrasonic echo response signal to be frozen for analysis and observation by an operator and (2) the use of a visual graphic feedback indicator is superimposed on a frozen trace of the echo response signal display to show the operator the results of the analysis in comparison with this echo response signal. Other A-mode systems to date have either (1) not provided any graphical display of the analysis results to the user, only a digital readout of the fat/loin depth condition or (2) provided a display of the signal but with no provision for freezing the signal for automated analysis.

SUMMARY OF THE INVENTION

It is an object of the present invention to employ an image freezing switching unit for an ultrasonic backfat measuring apparatus which when actuated will indicate whether or not the measuring apparatus has indicated an accurate reading of the depth of the backfat for the animal under measurement More specifically it is an object of the invention to employ this freezing switching unit which, when activated, determines if an inaccurate depth of fat measurement is present because (1) excessive noise has introduced high gain into this measurement, (2) low gain has caused the echo signal image to be of an undesired low amplitude and/or (3) the ultrasonic transducer was not held by the operator in a proper flush contact position with the skin of the animal under measurement.

It is an object of the invention when the aforementioned inaccurate measurement occurs to adjust the gain and/or position of the transducer in flush contact with the skin of the animal so that the switching unit can again be activated to thereby ascertain if the depth of backfat measurement is accurate.

It is another object of the present invention to provide the measuring and analyzing circuit and display unit employed in this depth of backfat measuring apparatus in a housing which is of a sufficiently small size that it can be held in one hand of an operator so the operator can easily read the value of the backfat on the display unit.

It is still another object of the invention to provide a casing for the freezing switching unit and the ultrasonic transducer which is also of sufficiently small size so that an operator can readily move the transducer along the skin of the animal while observing backfat depth reading on the display unit and readily close the switch with his thumb so that the accuracy of this reading can be ascertained by observing that the position of a graphical overlay indicator, that is generated by a backfat analyzing circuit, is through a desired position on the echo wave image.

It is still another object of the present invention to provide an apparatus to check the accuracy of a backfat depth measurement which requires very little training before the operator becomes skilled in the art of detecting such an inaccuracy.

The present invention provides a hand operated image freezing switching unit for enabling an operator to determine if the value of an animal's backfat being measured by an ultrasonic backfat depth measuring apparatus is accurate. This switching unit is advantageous when used with my ultrasonic apparatus and method for measuring animal backfat that is disclosed in my previously filed patent application Ser. No. 08/533,359, U.S. Pat. No. 5,613,493.

DETAILED DESCRIPTION OF THE INVENTION

Figure 1:
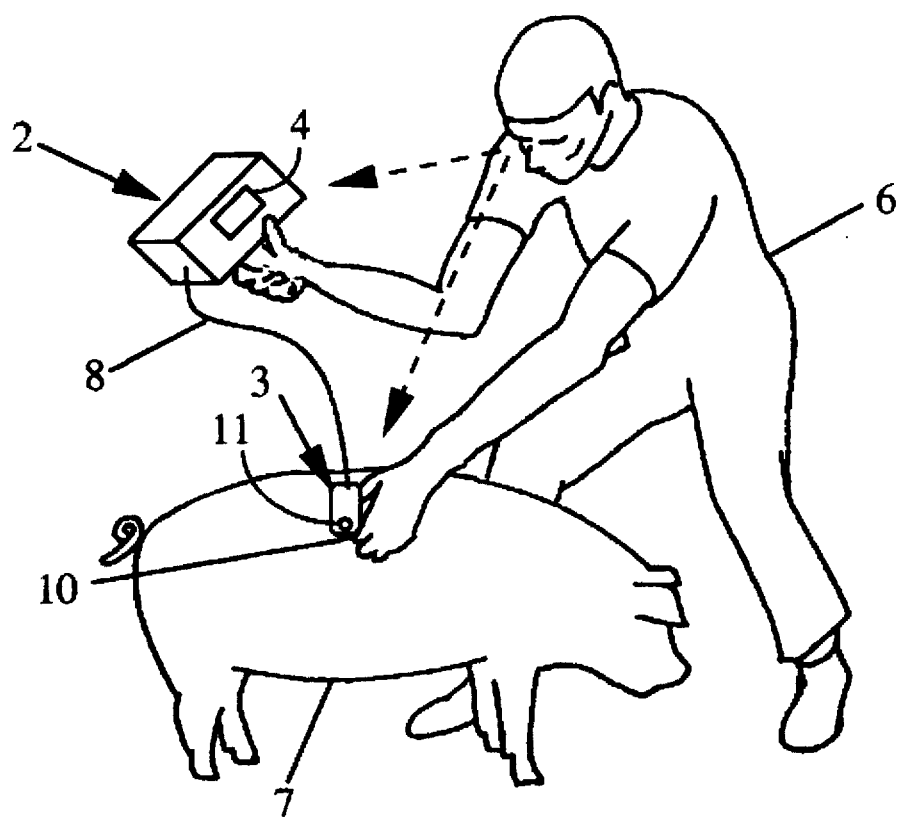
FIG. 1 is a view showing an operator conveniently holding a casing containing an ultrasonic transducer and the unique image freezing switching unit in one hand while conveniently holding a backfat measuring-analyzing circuit and display unit in the other while making a visual check of the accuracy of a backfat reading.
Figure 2:
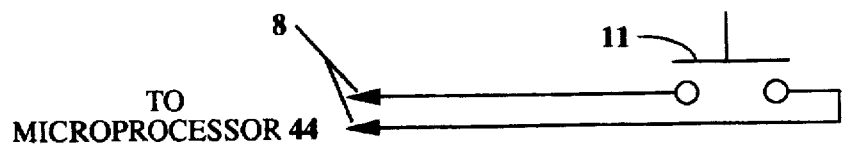
FIG. 2 shows a view of the switching unit.
Figure 3:
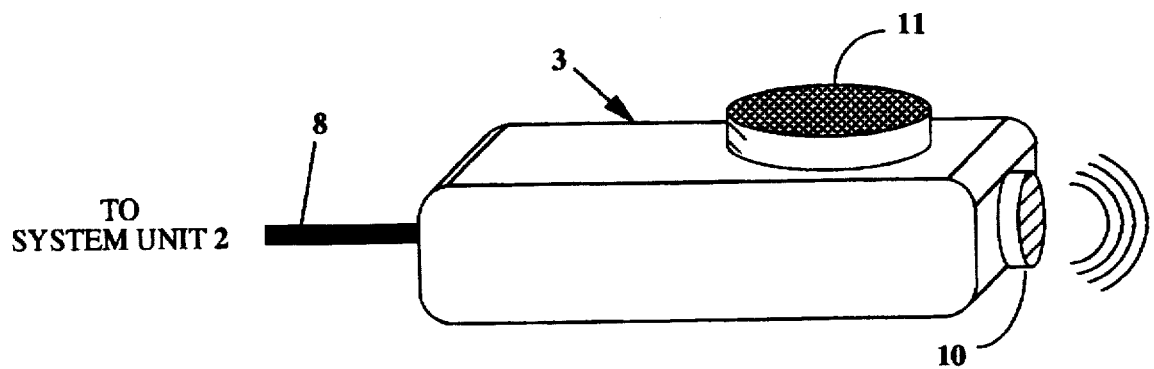
FIG. 3 shows how the switching unit and ultrasonic transducer are retained within a unitary casing.
Figure 5:
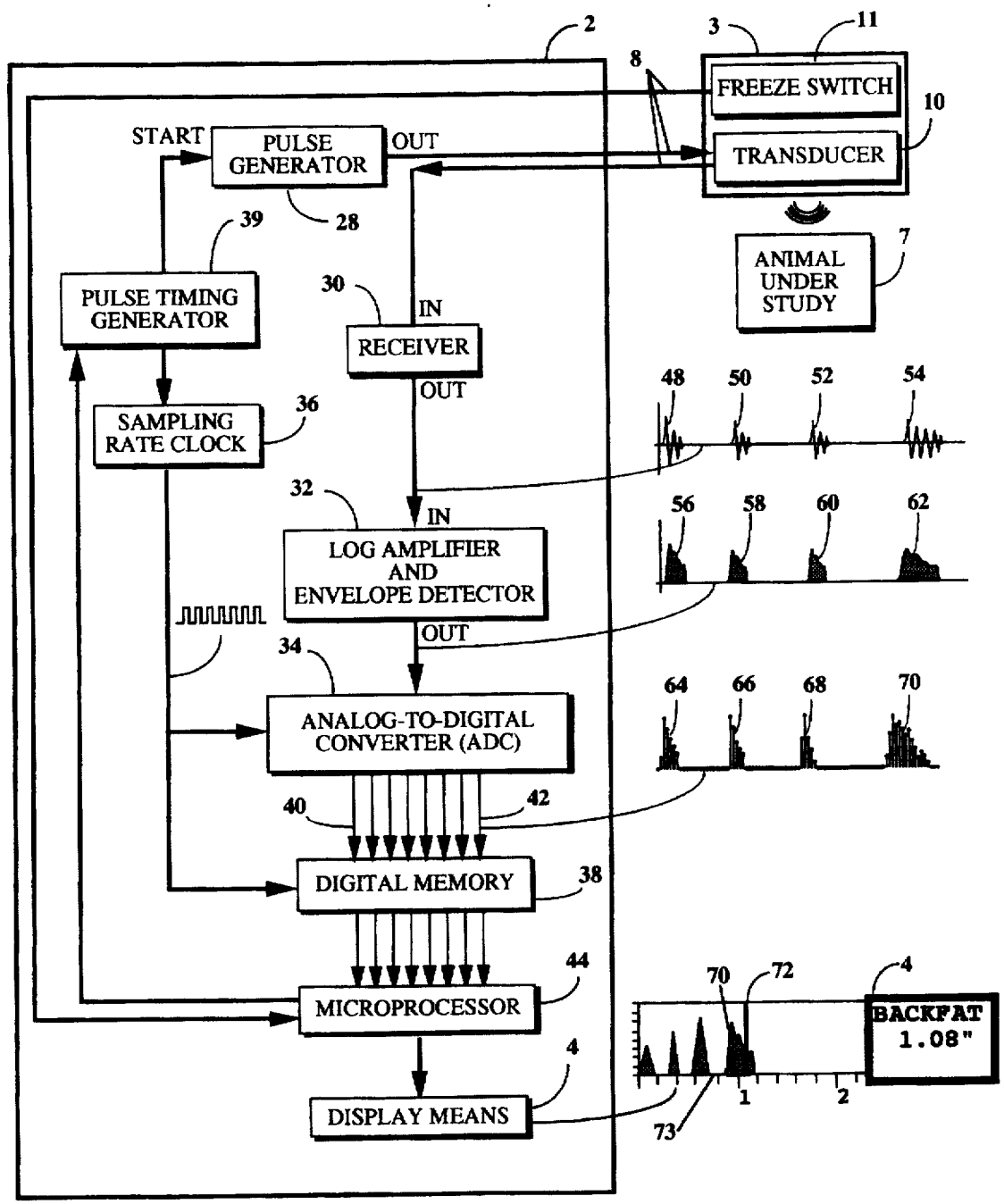
FIG. 5 is a block diagram showing how the unique image freezing switching unit is employed with previously mentioned backfat analyzing and measuring circuits.

FIG. 1 shows a housing 2 containing a backfat measuring and analyzing circuit as shown in FIG. 5 and a casing 3. A display means 4 is shown mounted on the side of the housing 2 and the size of the housing 2 is such that it can be held in one hand of an operator 6 who is shown taking a backfat measurement of an animal such as a hog 7. This FIG. 1 also shows a flexible electrical connection 8 extending from one end of the housing 2 into the casing 3 as is best shown in FIG. 3 The casing 3 contains an ultrasonic transducer 10 and an image freezing switching unit 11 in the form of a signal pole single throw momentary contact mechanical push button as is best shown in FIGS. 2 and 3.

In order to understand how the present invention of a unique image freezing switching unit is used to check the accuracy of a backfat measuring and analyzing apparatus, the following material describing my aforementioned Ultrasonic Apparatus and Method for Measuring Animal Backfat patent application appears to be in order.

Figure 4:
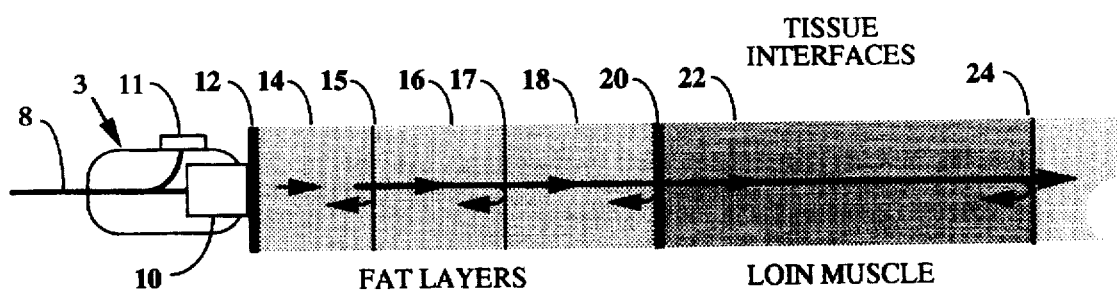
FIG. 4 is a sectional view through a portion of an animal's back with the transducer probe in place.

FIG. 4 shows a typical cross sectional view of the backfat and loin of an animal such as the hog 7 shown in FIG. 1. The ultrasound transducer 10 is applied to the outer intact skin surface 12 of the animal, with a coupling fluid such as oil. As shown in FIG. 4, the transducer emits and receives ultrasound pulses which reflect from the various tissue layers within the animal. The first fat layer 14 is typically six to ten millimeters in depth and is separated from the second fat layer 16 by a thin membrane 15. Similarly, the second and third backfat layers 16 and 18 are separated by a thin membrane 17. The third or additional backfat layers only appear in certain species and breeds and at certain ages and weights. Thus the number and thicknesses of the different fat layers can change significantly from one animal to another, from one breed to another and by species. The border between the last fat layer 18 and the beginning of the loin muscle 22 is denoted as 20. FIG. 4 identifies an interface 24 between the loin muscle 22 and a backbone, not shown. The backbone and the animal's rib bone, not shown, can be used to provide orientation of the loin muscle. The measuring and analyzing apparatus shown within the housing 2 shown in FIGS. 1 and 5 accurately quantifies the depth to the beginning of the loin muscle 22 or, in other words, the bottom of the interface 20 by analyzing the ultrasound signals reflected back to transducer 10.

FIG. 4 shows an apparatus to accurately quantify the depth to the beginning of the aforementioned loin muscle 22 or, in other words, the bottom of the interface 20 by analyzing the ultrasonic signal reflected back to transducer 10. A pulse generator 28 as shown in FIG. 5 is used to excite the ultrasound transducer 10. The transducer 10 emits an A-mode ultrasound wave into the tissue and this ultrasound energy in the form of an echo signal is reflected back to the transducer 10 at each tissue interface 15, 17 and 20 as shown in FIG. 4. As shown in FIG. 5 the signals received at the transducer 10 are logarithmically amplified and enveloped by detector 32 before being converted into a fully digital form by the analog to digital converter, ADC, 34. The sampling rate of the ADC 34 is set by a clock circuit 36 which establishes the temporal resolution of the system. Since in this type of system, travel time of the ultrasonic wave is related to travel distance, the clock 36 also sets the spatial resolution of the system. The time duration of the transmitted pulse is thus also a factor of the spatial resolution. The clock circuit 36 also sequences the digital memory circuit 38. The clock is started at the same time as the transmitting pulse so there is proper time synchronization. The exact number of clock cycles and thus the size of the digital memory circuit 38 depends upon the sampling rate and the desired depth of tissue to be measured. FIG. 5 shows a number of electrical connections; e.g., 40, 42 between the ADC 34 and the digital memory 38 to represent the number of bits and resolution of the ADC. At least six bits of resolution are required and eight bits are generally desired in utilizing this system. Because the clock 36 is synchronized with the pulse generator 28 and the clocking frequency is known, then each sample within the digital memory 38 corresponds to a specific time from the time of the ultrasonic waveform Thus, each sample within the digital memory corresponds to a specific depth within the fat layers forming the backfat of the animal. The depth and the time are related by the speed of sound in the backfat which is generally taken at 1540 meters per second.

Once a single received waveform is stored in the digital memory 38, it is read and analyzed using the microprocessor 44 which can; for example, be a 8051 family of microcontrollers; for instance, the DS80C320 from Dallas Semiconductor. The microprocessor 44 drives a display means 4 which communicates the results of the measurements to the user. The display 4 is a full graphic display of the waveform and may be implemented using a graphic LCD display such as the HG 24501 from Hyundai Electronics.

Figure 6:
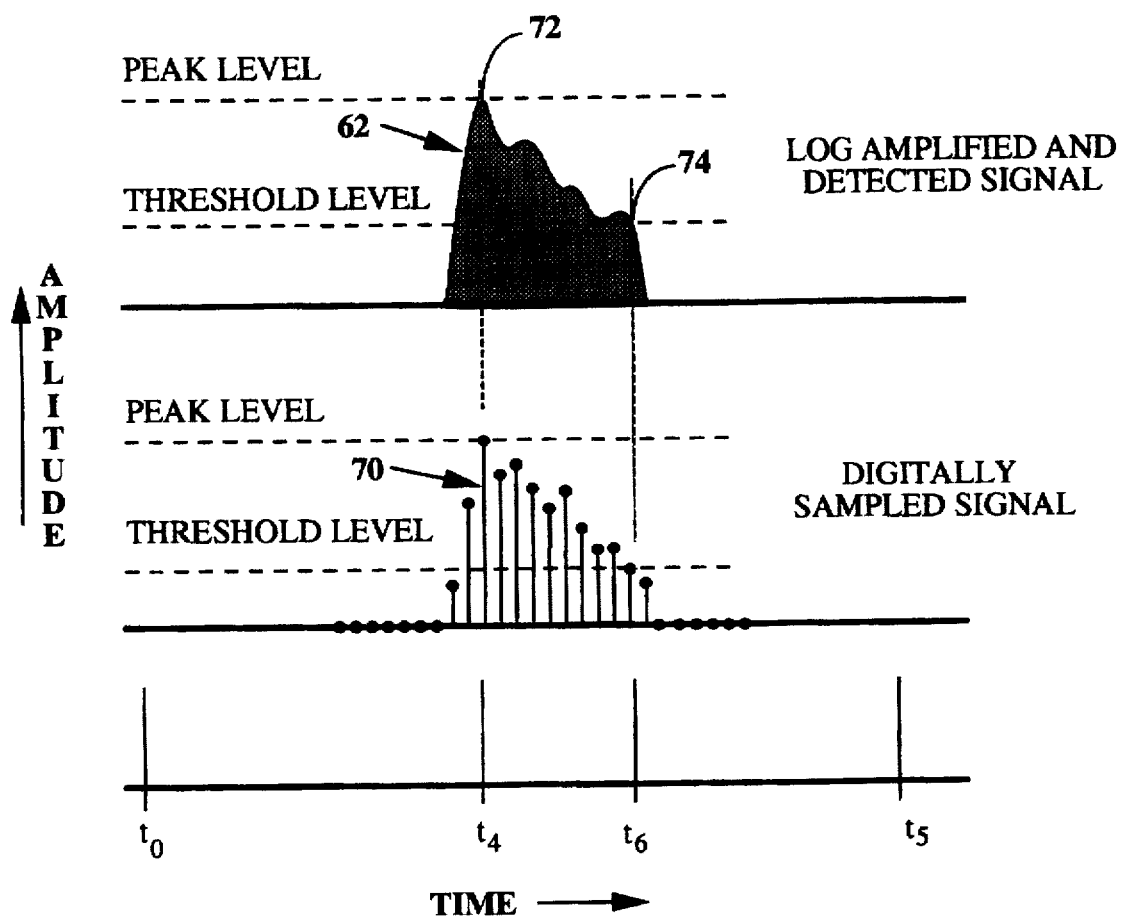
FIG. 6 shows in graphic form how the apparatus within the housing 2 and the transducer 10 within the casing 3 as shown in FIG. 5 determines the depth of backfat of an animal.

In order to explain further how the apparatus functions, reference is now made to FIG. 5. The trace shown in the upper portion of FIG. 5 represents the received ultrasound signals 48, 50, 52 and 54 as a function of time as produced by the receiver circuit 30 as a result of the signal it receives from the transducer 10. The trace shown in the lower portion of FIG. 5 shows the log amplified and detected signals 56, 58, 60 and 62 correspond to the reflection of the interface between the animal's skin 12 and fat layer 14 and interfaces 15, 17 and 20 respectively as shown in FIG. 4. After logarithmic amplification and detection, the signals which correspond to 48, 50, 52 and 54 are 56, 58, 60 and 62 respectively are in turn converted into the digitally sampled signals 64, 66, 68 and 70 shown in FIG. 5. It can be seen that the signals 54 and 62 are of extended time duration relative to the other signals. FIG. 6 shows how to repeatedly and reliably determine the extent of signal 62 and thus, the exact point of the beginning of the loin muscle 22 or, in other words, the depth of maximum backfat at interface 20 as shown in FIG. 4. The apparatus as shown in FIG. 5 thus correctly identifies the signal which corresponds to interface 20 irrespective the number of intervening fat layers.

FIG. 6 further shows an expanded view of the signal 62 and time interval $t_4$ to $t_5$. The apparatus shown in FIG. 6 starts by examining the signal in reverse time order; that is, from $t_5$ to $t_4$. Time $t_5$ is selected by previous experimentation for the specific species of animal to be measured and is such that it will always be located at a point beyond the deepest fat thickness of that species. Experimental research has determined that for market hogs in the weight of two hundred to two hundred eighty pounds, the deepest backfat thickness is 2.4 inches and therefore, this $t_5$ as shown in FIG. 6 is set to a time corresponding to 2.5 inches. Starting at time $t_5$ in FIG. 6 and working toward time $t_0$, the echo signal 62 becomes the first echo, thus removing the ambiguity caused by the variability in the number of echoes such as 58 and 60 shown in FIG. 5. The apparatus shown in FIG. 5 next performs a search for a peak of the echo signal 62 and finds the point labeled 72 as identified in FIG. 6. Once this point 72 is located and this peak level is found, the apparatus of FIG. 5 next searches back in the direction of $t_5$ until the signal level falls below a threshold level as indicated by reference numeral 74. This threshold level is taken as a percentage of the peak level. In this way, variations in the absolute signal level are not important since the threshold is always set as a percentage of the peak level. The particular percentage of the peak level employed for hogs has been found through experimentation to be 30%. This percentage was found to best represent the true fat/muscle interface when compared to actual carcass data measurements.

Figure 7:
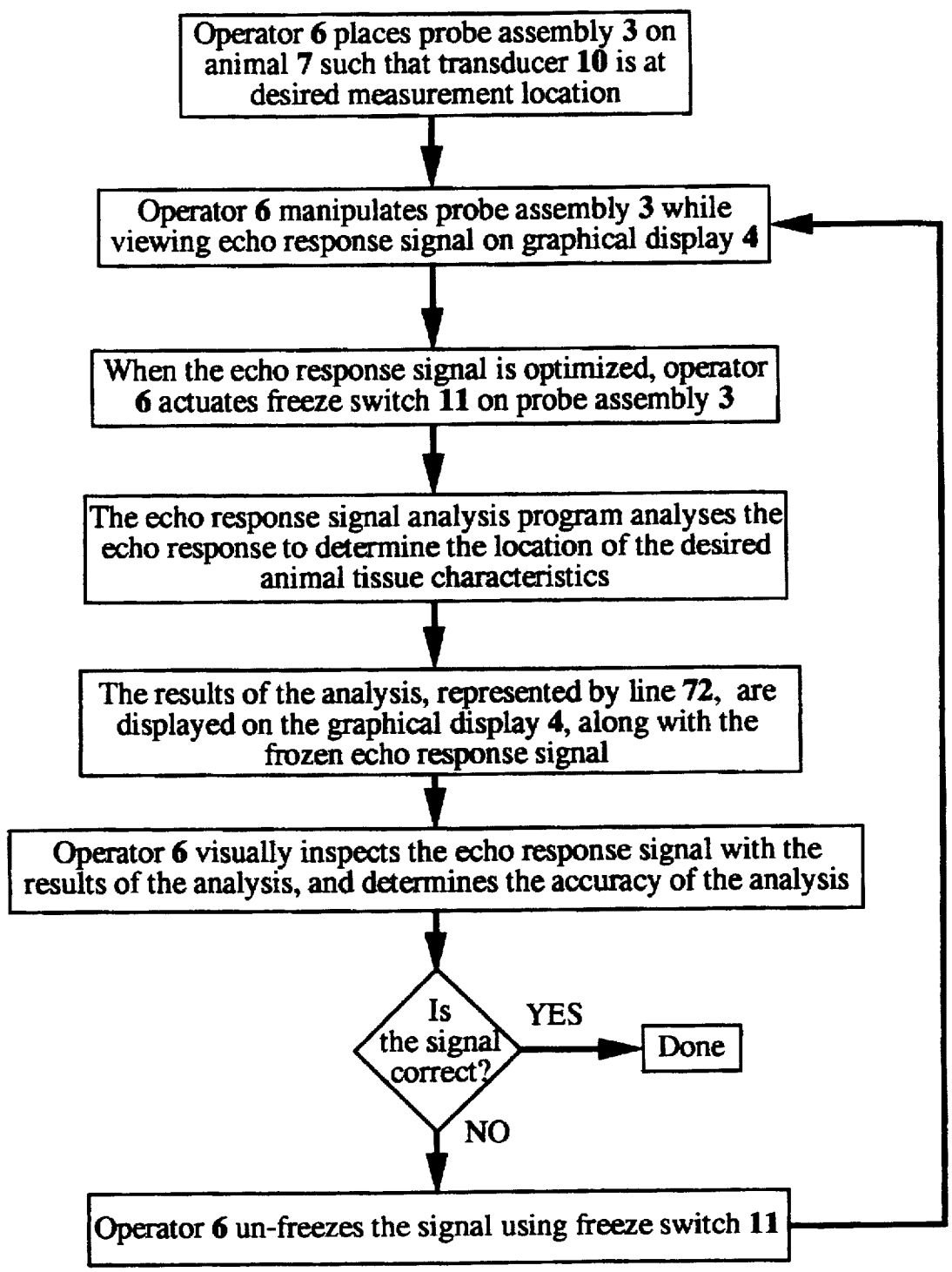
FIG. 7 shows the sequential steps the apparatus of FIG. 1 takes in ascertaining that the accuracy of the measured depth of backfat under measurement is correct.

FIG. 7 clearly shows the most important steps in the order of execution which components of the apparatus shown in FIG. 5 employs to determine the accuracy of a backfat depth measurement of an animal which was produced by the measuring and analyzing apparatus shown within the housing 2 in FIG. 5

Figure 8:
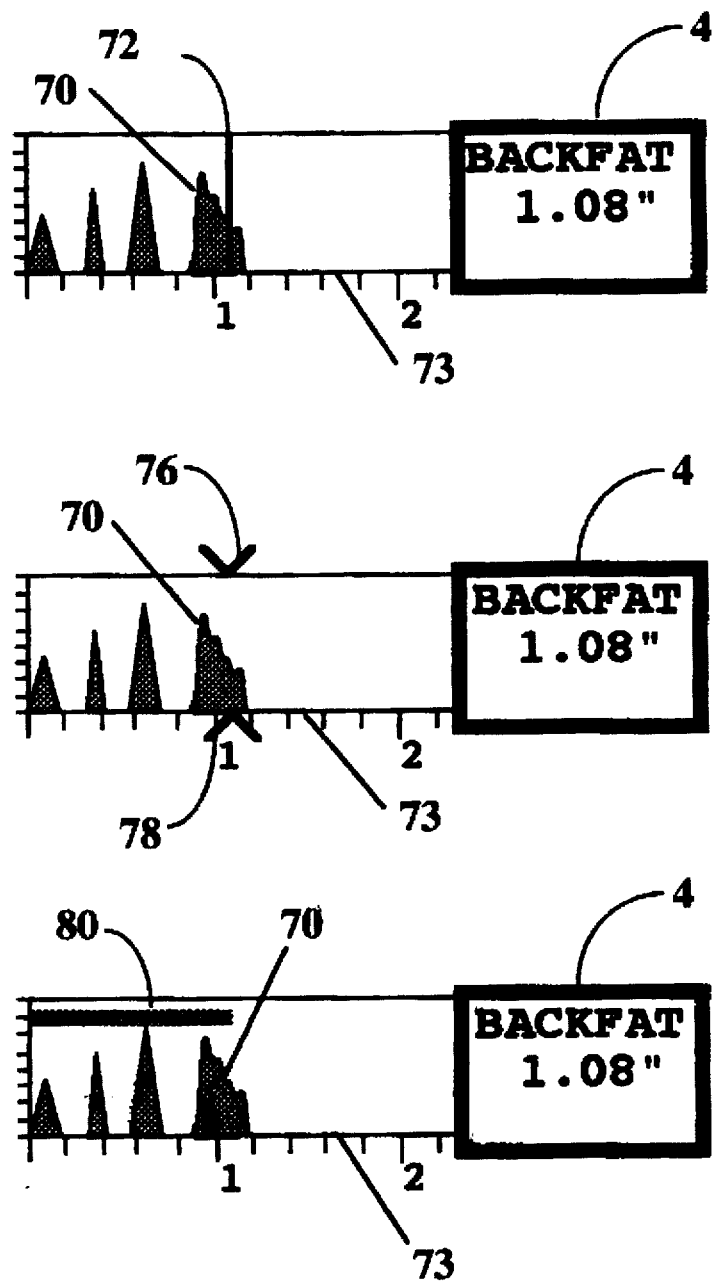
FIG. 8 show three types of unique graphical overlay indicators that can be used to ascertain if a backfat measurement is accurate.

FIG. 8 shows three different forms of graphical overlay 72; 76, 78; and 80 for the display unit 4 that is generated by microprocessor 44 shown in FIG. 5 when checking the accuracy of the depth of backfat reading on the display unit 4 by the closing of the image freezing switching unit 11. The microprocessor 44 accomplishes this by generating the appropriate instructions to the graphical LCD display module to produce line 72, arrows 76 and 78, or bar 80, at the desired location. The exact form of the marker is programmed into the microprocessor using standard software. The top illustration of FIG. 8 shows that the graphical overlay indicator is in the form of a vertical line 72 that passes through a value of 1.08 on the linear scale 73. This value is shown to be 30% of the peak of the first strongest innermost echo wave image 70 that is transmitted from the loin interface of the animal by way of the ultrasonic transducer 10 to the microprocessor analyzing circuit 44. Since the operator 6 can readily see that the position of the graphical overlay indicator 72 passes through the correct portion of the strongest echo wave signal 70 as noted above, the operator can conclude that a reading of the value of the backfat which has been measured is accurate. The middle illustration of FIG. 8 alternatively shows that the graphical overlay indicator is in the form of a pair of arrows 76, 78. One of these arrows 76 is located above and points downwardly to the value of 1.08 on the backfat depth scale 73 and the other arrow 78 is positioned immediately below the first arrow and points in an upward direction to the same value of 1.08 on the scale 73. The bottom illustration shown in FIG. 8 discloses still another alternative backfat depth indicator 80 that can be used. In this case the graphical overlay indicator 80 is in the form of a horizontal bar that extends across and above a portion of the backfat scale 73. To read this value on the backfat scale 73 the operator merely notes the reading on the scale that is immediately below the terminating right end of the bar that forms this graphical overlay indicator 80.

Figure 9:
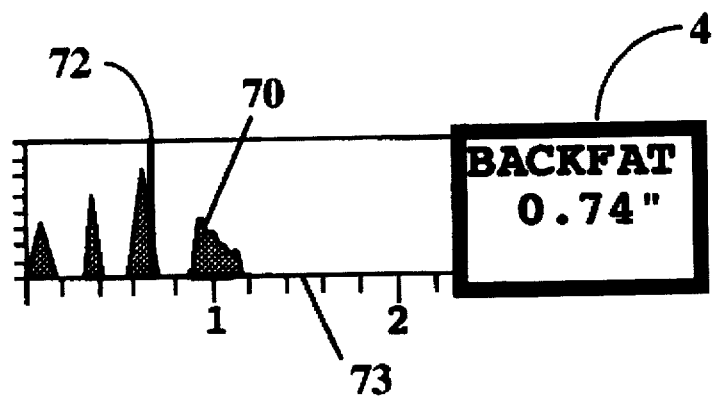
FIG. 9. shows three different positions of the unique graphical overlay indicator on the peak images of three display units all of which indicate that the measurement of the measuring and analyzing units are inaccurate.
Figure 9:
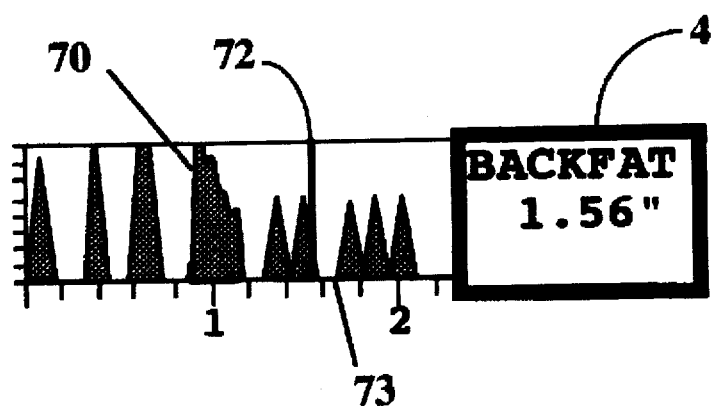
Figure 9:
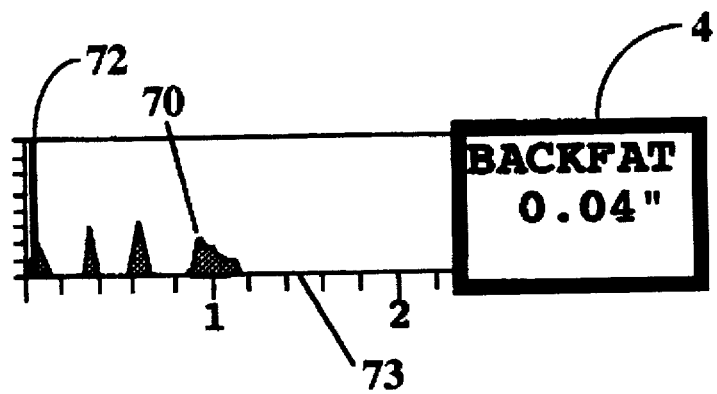

FIG. 9 shows examples of signals which are considered inaccurate signals. These illustrations should be compared to a signal that is accurate for a given animal such as that shown in FIGS. 5 and 8. In the top illustration of FIG. 9, the signal pattern shows that the measuring and analyzing apparatus in housing 2 has identified the third of the four signals as indicated by the vertical line 72. However, timewise there is clearly a signal taken from a point within the animal that is deeper than that indicated, although the alignment or gain setting is such that this signal is not of sufficient amplitude to be recognized by the measuring and analyzing apparatus in housing 2. Under these circumstances the operator 6 in FIG. 1 would be aware of the incorrect reading by noting the deeper signal and would repeat the testing with a different alignment of the transducer 10 against the outer skin of the animal or with a different gain setting. The middle illustration shows the result of excessive signal gain in which a number of signals exceed the screen display size and are "clipped" while other noise signals have appeared where none were shown earlier. The measuring and analyzing apparatus in housing 2 in this case has incorrectly identified a noise impulse gain shown by the vertical line 72. In this instance the operator 6 would repeat the measurement with a lower again setting. In the bottom illustration there is too little signal gain and the measuring and analyzing apparatus in housing 2 has not recognized any of the signals because; for example, they do not meet the proper threshold criteria. In this case the vertical line 72 may default to some fixed location, or other location depending upon the measuring and analyzing apparatus. In this case the operator 6 would repeat the measurement with increased signal gain.

Summarizing, it can be seen that an ultrasound image freezing apparatus has been disclosed for a backfat measuring instrument the freezing portion of which is of sufficiently small size that it can be readily supported in one hand of an operator while the instrument is held in the other hand of the operator and which simultaneously allows the operator to observe the position of a graphical overlay indicator over an echo response signal in order to determine if it passes through the strongest echo wave signal 70. The simplest arrangement of the freezing apparatus and measuring instrument reduces the time it takes for a new operator to learn how to determine if the depth of fat value being produced by the measuring instrument is accurate.

This ultrasound image freezing apparatus has the additional advantage in that the freezing apparatus employs a push button switch on the outer surface of a casing containing an ultrasonic transducer which an operator can close by depressing it with his thumb while the transducer is in contact with the skin of an animal to determine if the value shown on a graphical overlay indicator, that is generated by a backfat analyzing circuit, passes through the strongest echo wave signal and to thereby ascertain if its depth of backfat indication is accurate. If the indication is shown to be inaccurate, the transducer would then be repositioned against the animal and/or a different gain setting would be effected in the analyzing circuit.

What is claimed is:

1. An ultrasonic backfat measuring apparatus for an operator to accurately measure in a reverse time manner the maximum amount of backfat in an animal comprising a housing containing a pulse generator and a measuring-analyzing circuit and a backfat display unit for holding in one hand of said operator that is performing said measurement, an ultrasonic transducer and an image freezing switching unit mounted in a casing for holding in the other hand of said operator, said transducer being engageable with the outer skin of said animal whose backfat is to be measured, an electrical connection between said pulse generator and measuring circuit and said backfat display unit in said housing, said transducer being operable to receive an ultrasonic wave signal from said pulse generator for transmitting through the skin of said animal and to transmit a responding echo wave signal to said transducer and by way of an electrical connection to said display unit for recording said echo wave signal thereon, said transducer being operable for movement along the skin of the animal until the operator simultaneously sees a strong echo image along a backfat depth-time line and a digital backfat reading on said display unit that represents the depth of the innermost loin/fat interface of the animal, said image freezing switching unit being operable to freeze said image of said echo wave signal and digital reading on the display unit, said analyzing circuit being operable to analyze the measurement of said frozen echo wave signal and to place a graphical overlay indicator over said image of said echo wave signal and along said backfat depth-time line of said display unit so that the operator can visually determine if the digital reading is accurate by ascertaining that the graphical overlay indicator passes through the strongest image of said echo wave signal.

2. A hand operated image freezing switching unit to enable an operator to readily determine if the value of an animal's backfat that is being measured in a reverse time manner by an ultrasonic transducer and a unitary measuring and analyzing unit and that is being recorded in digital form and in an echo wave image form along a backfat depth scale of a display unit is accurate, said image freezing switching unit being spaced from and electrically connected by a flexible cable to said analyzing unit said analyzing unit being operable to send a signal to said display unit to form a graphical overlay indicator over said echo wave image when said switching unit is closed and said overlay indicator providing the operator with a backfat reading on said backfat depth scale to determine if the echo wave image indicator is over the strongest echo wave and to thereby indicate that the indicated backfat measurement is accurate.

3. The ultrasonic backfat measuring apparatus claim 2 wherein said switching unit is a manually operated simple momentary contact mechanical push button.

4. The ultrasonic backfat measuring apparatus of claim 2 wherein the transducer and said freezing switching unit are retained in a casing and wherein the transducer extends outwardly from one end of the casing and the switch extends through a top portion of said casing that is adjacent to the end of the casing containing said transducer.

5. The ultrasonic backfat measuring apparatus of claim 2 wherein a casing is employed that is a rectangularly shaped configuration and said freezing switching unit and transducer are located at one of its end portions and the opposite end portion is of sufficient size for holding in the hand of said operator.

6. The ultrasonic backfat measuring apparatus of claim 2 wherein a housing is employed that is of a rectangularly shaped configuration and wherein said digital display and echo wave signal display are adjacent one another in said housing and a scale representing the depth to which said ultrasonic signal traveled into the innermost fat/loin interface is located below the location where the echo wave signal is displayed.

7. The ultrasonic backfat measuring apparatus of claim 2 wherein the graphical overlay indicator is a vertical line passing through the echo wave image.

8. The ultrasonic backfat measuring apparatus of claim 2 wherein the graphical overlay indicator consists of a pair of arrows wherein one of said arrows is positioned above and pointing down to the backfat depth scale of the display unit and the other arrow is positioned immediately below the first arrow and points in an upward direction to the backfat depth scale to indicate the measurement of the depth of the backfat thereon.

9. The ultrasonic backfat measuring apparatus of claim 2 wherein the graphical overlay indicator consists of a horizontal bar whose length extends across and above a portion of the backfat depth scale so that the number on the scale immediately below the terminating end of said bar indicates the measurement of the depth of backfat thereon.

10. An image freezing switching unit to enable an operator to check the accuracy of a system that employs a reverse time approach to measure and indicate the thickness of backfat in an animal that employs a means to transmit a digital control signal to a pulse timing generator which synchronizes the transmitting and receiving functions of the system, and wherein said generator is operable to convert said digital control signal into a high voltage excitation and wherein a transducer connected to said generator is employed to convert said last mentioned signal into an ultrasonic wave signal and to transmit said wave signal through the outer skin and backfat of said animal and then off the backfat/loin interface and wherein a receiver is employed to amplify the responding ultrasonic echo signal reflected from the backfat/loin interface and to convert said echo signal back to an electrical signal and wherein a log amplifier and envelope detector is employed to further amplify said last mentioned electrical signal in a logarithmic manner and an analog to digital converter is employed to convert said last mentioned signal into a digital signal and wherein a sample rate clock is employed to regulate the rate by which said last mentioned signal is sampled by the analog to digital converter and wherein said clock is connected to a pulse timing generator for synchronization therewith and to a microprocessor by way of a digital memory circuit and wherein said microprocessor is operable to measure the peak of said last mentioned signal that is representative of the maximum amplitude of the response signal that is generated by said fat/loin interface and wherein the microprocessor is further operable to select a prescribed point on the trace of said responding signal that is below said peak that represents an accurate measurement of the depth of backfat and wherein a display means is operably connected to said microprocessor for visually indicating in digital form the thickness of backfat in said animal, and wherein said image freezing switching unit is comprised of a casing that is in spaced apart relationship to said system and contains a switch and said transducer mounted in and protruding from said casing, an electrical connection between said switch and said microprocessor, said switch when actuated being operable to freeze said image of said ultrasound trace containing said peak signal on said display means and said microprocessor being operable to send a signal representing an accurate measurement of said backfat in the form of a graphical overlay indicator that identifies a point on the trace of said peak displayed on said display means when said switching unit is frozen and to thereby determine the accuracy of the backfat measurement.

* * * * *